United States Patent [19]

Schaller

[11] Patent Number: 5,555,890
[45] Date of Patent: Sep. 17, 1996

[54] PHARYNGEAL END-TIDAL CARBON DIOXIDE MEASURING CATHETER

[75] Inventor: Douglas A. Schaller, Hermosa Beach, Calif.

[73] Assignee: University of Southern California, Los Angeles, Calif.

[21] Appl. No.: 202,859

[22] Filed: Feb. 25, 1994

Related U.S. Application Data

[63] Continuation of Ser. No. 895,513, Jun. 8, 1992, abandoned.

[51] Int. Cl.⁶ ..................................................... A61B 5/08
[52] U.S. Cl. ............... 128/719; 128/205.12; 128/205.28; 128/206.11
[58] Field of Search ..................................... 128/716, 719, 128/730, 205.27, 205.28, 206.11, 207.14, 207.18, 205.12; 600/156, 138

[56] References Cited

U.S. PATENT DOCUMENTS

| | | |
|---|---|---|
| 3,613,665 | 10/1971 | Gorsuch . |
| 4,220,162 | 9/1980 | Clark et al. . |
| 4,221,130 | 9/1980 | Burrows . |
| 4,300,550 | 11/1981 | Gandi et al. ........................ 128/207.18 |
| 4,329,995 | 5/1982 | Anthracite . |
| 4,423,739 | 1/1984 | Passaro et al. . |
| 4,446,864 | 5/1984 | Watson et al. ....................... 128/207.14 |
| 4,549,553 | 10/1985 | Hochberg . |
| 4,619,269 | 10/1986 | Cutler et al. . |
| 4,677,987 | 7/1987 | Choksi .................................... 128/719 |
| 4,821,715 | 4/1989 | Downing ............................. 128/207.18 |
| 4,821,736 | 4/1989 | Watson . |
| 4,981,477 | 1/1991 | Schon et al. . |

Primary Examiner—William E. Kamm
Assistant Examiner—Jeffrey R. Jastrzab
Attorney, Agent, or Firm—Robbins, Berliner & Carson

[57] ABSTRACT

A catheter for measuring a fluid in a patient, such as end-tidal $CO_2$, having a proximal end, a proximal portion adjacent the proximal end, a distal end, a distal portion adjacent the distal end and a lumen therethrough. The distal end is adapted to terminate in the pharynx of the patient when the catheter is inserted through the patient's nasal passage. The proximal end is attached to a device for measuring the fluid. Fluid is measured as it passes from the pharynx, through the catheter and then into the measuring means.

4 Claims, 1 Drawing Sheet

PHARYNGEAL END-TIDAL CARBON DIOXIDE MEASURING CATHETER

This is a continuation of Ser. No. 07/895,513, filed Jun. 8, 1992, now abandoned.

BACKGROUND OF THE INVENTION

This invention relates to the medical arts. In particular, it relates to an apparatus for measuring fluids such as end-tidal carbon dioxide and a method for using the same.

In numerous clinical settings, such as under anesthesia or during artificial respiration, it becomes desirable to monitor the carbon dioxide concentration in the arterial blood gas of a patient. Invasive procedures have been designed for accomplishing this, which include periodic blood sampling of arterial blood gas and the use of an in-dwelling catheter capable of directly monitoring the carbon dioxide concentration. The fact that such techniques are invasive subjects them to all the problems usually associated with such procedures, including the increased risk of infection, thrombosis, etc.

It is known that the carbon dioxide concentration of the last gas expired from the lung (alveolar or end-tidal gas) in normal breathing is related to the carbon dioxide concentration of arterial blood gas. In a single exhalation cycle, the first portion of such mixture exhaled by the patient consists principally of ambient air in passageways between the point of exhalation and the main airways of the lung. The first portion merges into the second portion of the exhaled mixture which consists of the residual ambient air and end-tidal gas (i.e., the gas contained in the cells of the lung). The last portion of the exhaled mixture consists principally of the end-tidal gas. This last portion of the exhaled mixture is of primary interest for diagnostic and analytical purposes.

Capnography is the monitoring of end-tidal carbon dioxide ($CO_2$) concentration. A capnometer measures the amount of carbon dioxide gas exhaled by a patient. Typically, a sampling tube is used to convey the sampled flow of gas from the air tube to the gas measuring means. The sampling tube can be connected to a sampling port located outside or just inside the external narier or, where a patient is fitted with an endotracheal tube, the sampling tube can be integral with the endotracheal tube. However, medical instruments relying upon such tubes are not as accurate or as versatile as might be desired.

It is an object of the present invention to provide improved apparatus and methods for use in the measurement of a fluid in a patient.

SUMMARY OF THE INVENTION

In accordance with the present invention, there is provided a catheter for measuring fluids, such as end-tidal $CO_2$, in a patient. The catheter has a proximal end, a proximal portion adjacent the proximal end, a distal end, a distal portion adjacent the distal end and a lumen therethrough. The distal end is adapted to terminate in the pharynx of the patient when the catheter is inserted through the patient's nasal passage.

In one embodiment of the invention, the distal portion is formed of a rigid material and shaped to substantially conform to the patient's nasal passage. In another embodiment of the invention, the distal portion is integrally attached to and coaxial with a nasogastric tube, while the proximal portion diverges away from the nasogastric tube.

In a method for monitoring a fluid in a patient in accordance with the invention, the distal portion is inserted through the patient's nasal passage and the distal end is positioned in the patient's pharynx, while the proximal end is attached to a means for measuring the fluid. Fluid is then measured as it passes from the pharynx, through the catheter and then into the measuring means.

BRIEF DESCRIPTION OF THE DRAWINGS

The invention may be better understood with reference to the accompanying drawings, in which.

DETAILED DESCRIPTION OF PREFERRED EMBODIMENTS

Figure 1:
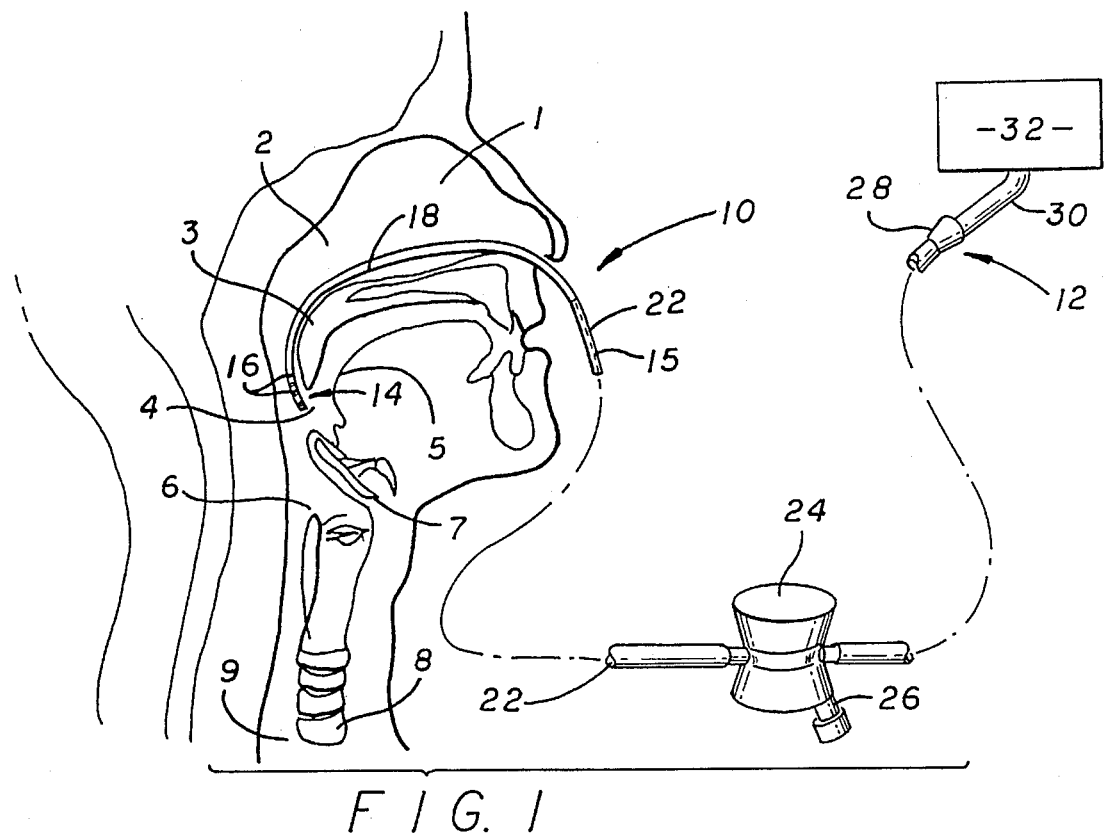
FIG. 1 is a perspective view of one embodiment of a pharyngeal end-tidal carbon dioxide monitoring catheter in accordance with the invention, showing the catheter inserted into the patient.

Referring now to FIG. 1, there is shown a pharyngeal catheter 10 in accordance with the invention as it would be inserted into the patient. The catheter runs through the patient's nasal cavity 1 and nasopharynx 2, above the soft palate 3. The catheter 10 has a proximal end 12, a distal end 14 and a lumen 15 therethrough. The distal end 14 of the catheter 10 contains a plurality of gas intake ports 16. As illustrated, the catheter 10 continues through the nasopharynx 2 into the oropharynx 4. Behind the base of the tongue 5, the laryngopharynx 6 joins the oropharynx 4; the distal end 14 of the catheter 10 is generally located to the extent possible at or near the junction of the oropharynx 4 and the laryngopharynx 6. Thus, the distal end 14 of the catheter 10 would be located above the epiglottis 7, trachea 8 and esophagus 9.

The catheter 10 typically has a diameter of from about 2 mm to about 4 mm, preferably from about 2 mm to about 3 mm, and most preferably about 2.5 mm. The gas intake ports 16 typically have a diameter of from about 1 mm to about 3 mm, preferably from about 2 mm to about 2.5 mm, and most preferably about 2 mm.

Adjacent to the distal end 14 is a distal portion 18 adapted to pass through a patient's nose into the opening of the patient's nasopharynx, so that the gas intake ports 16 are positioned in the patient's pharynx when the catheter is inserted into a patient. The distal portion 18 is formed of a relatively rigid material, such as polyvinyl chloride or polyethylene. It is molded so that it substantially conforms to the contours of the patient's nasal passage and so that the distal end 14 can be positioned at the opening of the internal nares, away from the posterior pharyngeal wall.

The proximal end 12 of the catheter 10 is adjacent to a proximal portion 22. It is made of a relatively flexible material, such as polyvinyl chloride or polyethylene containing a sufficient amount of one or more conventional plasticizer that it conforms to and can be easily attached to a patient's face and head. The region of the proximal portion 22 which extends beyond the face of the patient contains a suction trap 24 with a suction port 26.

The proximal end 12 of the catheter 10 has a fitting 28 operationally connected by an intake line 30 to a means for measuring the fluid 32. In the method in accordances with the invention, the distal end 14 is positioned in the opening of the patient's nasopharynx. The fluid to be measured enters into the catheter 10 through the fluid sampling ports 16, transverses through the length of the catheter, and enters the measuring means 32.

It is an advantage of the catheter 10 that the distal end 14 is positioned away from the posterior pharyngeal wall, where secretion accumulates, thus minimizing the problem of pharyngeal secretions clogging the intake line 30. The catheter 10 also contains a suction trap 24 and suction port 26, so that if any secretion is sucked into the catheter it is caught in the secretion trap and does not obstruct the intake line 30.

In a preferred embodiment, the fluid to be measured is end-tidal $CO_2$ and the means for measuring the fluid 32 is a $CO_2$ sensor, such as a capnograph. A representative capnograph is manufactured by Ohmeda (Madison, Wis.). While the preferred embodiment described herein utilizes a $CO_2$ sensor, other fluid sensors can obviously be used with the novel catheter described herein without departing from the scope of this invention.

Figure 2:
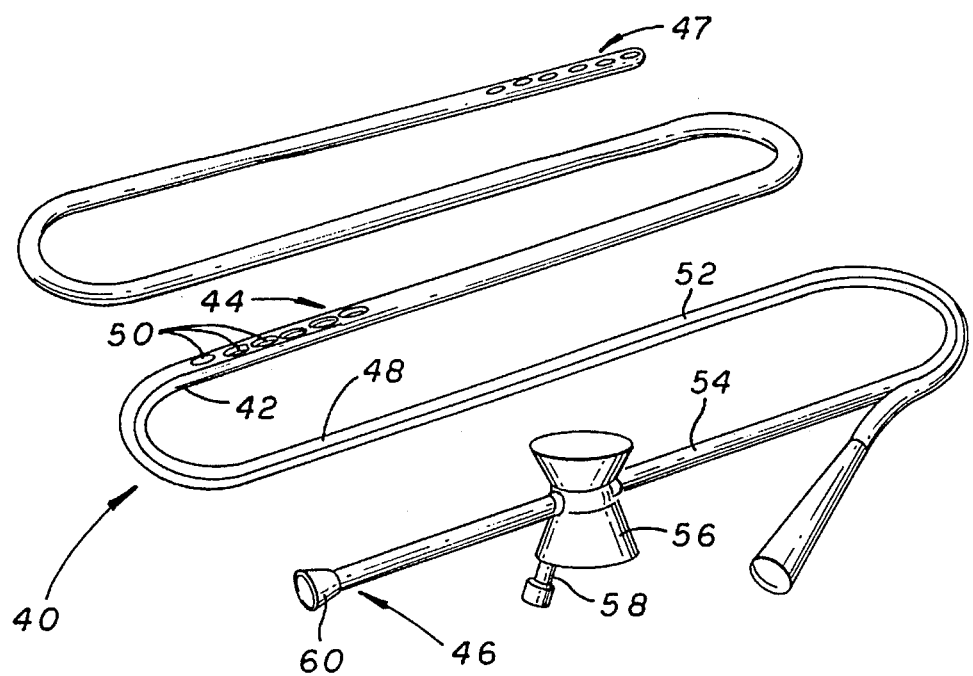
FIG. 2 is a perspective view of another embodiment of a pharyngeal end-tidal carbon dioxide monitoring catheter in accordance with the invention.

Referring now to FIG. 2, there is shown another embodiment of a catheter in accordance with the invention. The catheter 40 is integrally attached to a nasogastirc tube 42. The catheter 40 has a distal end 47, a proximal end 46 and a lumen 48 therethrough. Located between distal end 47 and proximal end 46 is sampling portion 44. The sampling portion 44 contains a plurality of fluid sampling ports 50.

Adjacent the distal end 44 is a distal portion 52 which is integrally attached to and coaxial with the nasogastric tube 42. The sampling ports 50 are adapted to be positioned in the pharynx of a patient, when the nasogastric tube 42 is inserted into a patient.

Adjacent the proximal end 46 is a proximal portion 54 which diverges from the nasogastric tube 52. The region of the proximal portion 54 which extends beyond the face of the patient contains a suction trap 56 with a suction port 58. The proximal end 46 of the catheter 40 has a fitting 60 operationally connected to an intake line to a means for measuring the fluid (not shown).

It is an unexpected advantage of the catheter in accordance with the invention that it can be used to accurately measure the ventilation of a patient under a wide variety of conditions. The catheter can be used while a patient is under mask general anesthesia. It is a further significant advantage of the invention that it can be used to monitor awake, sedated, non-incubated patients under regional anesthesia, during intensive care or during post operative recovery.

In a preferred embodiment of the inventive method, the nasal passage of the patient may be treated with a combination of a vasoconstrictor and a local anesthetic prior to insertion of the catheter. One particularly suitable combination contains 6–8% lidocaine [2-(diethylamino)-N-(2,6-dimethylphenyl)-acetamide] combined with an equal volume of ¼% phenlephrine hydrochloride for example, available from Winthrop Pharmaceuticals, New York, N.Y. under the designation Neo-Synephrine®), so as to provide a final solution which comprises about 3–4% lidocaine (about 30–40 mg/ml) and about ⅛% Neo-Synephrine® (about 1.25 mg/ml). A total volume of about 0.5–2 ml of the solution is applied to the nasal passage using a conventional nasal inhaler aerosol to provide a fine mist of the solution of the entire nasal passage. The inhaler is held just outside the external nares opening; the solution is sprayed to coat the nasal passage while the patient inhales through the nose. After the nasal passage has been treated, a short time interval (e.g., 5 minutes) is suitably allowed to elapse so as to permit the medication to anesthetize and vasoconstrict the passage prior to insertion of the catheter. Treatment of the nasal passage in this manner significantly reduces sensation in the nasal passage, allowing for insertion of the catheter without pain or discomfort. In addition, dilation of the nasal passage as a result of the vasoconstriction from the neosynephrine provides a wider path for insertion of the catheter; this facilitates insertion, reduces the possibility of nasal bleeding and decreases the amount of nasal secretions which could enter the catheter.

Depending upon the circumstances, other types of solutions comprising one or more vasoconstrictors and/or local anesthetics may be more suitable for use in facilitating insertion of the catheter. For example, a more dilute Neo-Synephrine® concentration should be used for patients with high blood pressure, because of the hypertensive effects of the drug once it is absorbed. For such patients, the Neo-Synephrine® solution employed to form the combined solution may be diluted by a factor of 1:1 to 4:1. Similarly, other vasoconstrictor or local anesthetic compositions may also be employed to provide suitable solutions.

The invention may be embodied in other specific forms without departing from its spirit or essential characteristics, and the foregoing preferred embodiments are to be considered in all respects only as illustrative and not restrictive.

What is claimed is:

1. A catheter for use in measuring gas concentrations in a patient, said catheter having a lumen therethrough, a proximal end, a distal end including a plurality of gas intake ports, a proximal portion including a suction trap, and a rigid distal portion adjacent the distal end dimensioned to be received in and substantially conform to a patient's nasal passage and to terminate at a location away from the patient's posterior pharyngeal wall.

2. A catheter in accordance with claim 1, wherein the distal portion is integrally attached to a nasogastric tube, and the proximal portion diverges away from the nasogastric tube.

3. A catheter in accordance with claim 2, wherein the nasogastric tube is coaxial with the distal protin.

4. A catheter in accordance with claim 1, wherein the gas intake ports have a diameter of from about 1 m to about 3 mm.

* * * * *